United States Patent [19]

Selbeck et al.

[11] 4,267,127
[45] May 12, 1981

[54] PROCESS FOR THE PRODUCTION OF PHOSPHORIC ACID TRIESTERS

[75] Inventors: Harald Selbeck; Claus Wulff, both of Krefeld; Uwe Hucks, Alpen; Erhard Tresper; Hugo Vernaleken, both of Krefeld, all of Fed. Rep. of Germany

[73] Assignee: Bayer Aktiengesellschaft, Leverkusen, Fed. Rep. of Germany

[21] Appl. No.: 60,679

[22] Filed: Jul. 25, 1979

[30] Foreign Application Priority Data

Jul. 29, 1978 [DE] Fed. Rep. of Germany ....... 2833341

[51] Int. Cl.³ .............................................. C07F 9/09
[52] U.S. Cl. .................................... 260/973; 260/966
[58] Field of Search .............................. 260/973, 966

[56] References Cited

U.S. PATENT DOCUMENTS

| | | | |
|---|---|---|---|
| 1,837,176 | 12/1931 | ter Horst | 260/974 |
| 2,653,161 | 9/1953 | Ballard et al. | 260/973 |
| 3,849,524 | 11/1974 | Collin | 260/949 |

Primary Examiner—Anton H. Sutto
Attorney, Agent, or Firm—Connolly and Hutz

[57] ABSTRACT

Phosphoric acid triesters of the formula

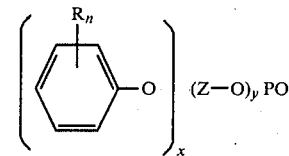

are produced in two or more stages by reacting phosphorus oxyhalides, phosphorus pentahalides, phosphoric acid monoester dihalides or phosphoric acid diester halides corresponding to the following general formula:

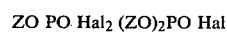

wherein Z is defined as above and Hal represents Cl and/or Br with at least one hydroxyaryl compound of the formula

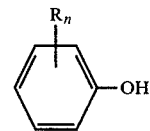

in a two-phase mixture of an organic solvent an aqueous alkaline earth metal and/or alkali metal hydroxide solution.

9 Claims, No Drawings

PROCESS FOR THE PRODUCTION OF PHOSPHORIC ACID TRIESTERS

Phosphoric acid esters of aliphatic alcohols and aromatic hydroxy compounds are widely used as plasticisers, lubricants and hydraulic fluids. The production of phosphoric acid esters such as these is known in principle and is described in detail in the literature (cf. inter alia Houben-Weyl, Vol. 12/2, Georg Thieme Verlag). The processes used in practice are, however, attended by distinct disadvantages. As can be seen from a number of patent applications and patents (for example, German Offenlegungsschrift No. 1,960,526, German Offenlegungsschrift No. 2,532,795, and U.S. Pat. No. 3,723,315), most of these phosphoric acid esters are today commercially produced by reacting the aliphatic alcohols or the aromatic hydroxy compounds with phosphorus oxychloride at elevated temperature in the presence of a catalyst. This requires a reaction temperature in the range of from 160° to 250° C. These high temperatures can result in discoloration of the reaction product, with the result that subsequent distillation of the phosphoric acid esters is essential if light-coloured products are to be obtained. In addition, secondary products are also formed at the high reaction temperatures applied and have to be separated off by distillation. Another serious disadvantage of this process is the evolution of gaseous hydrogen chloride which gives rise to problems of corrosion in the technical installations used. Another disadvantage is that the alcohol components and the aromatic hydroxy compounds both have to be used in an excess in order to obtain a high yield of phosphoric acid triesters.

In another process (W. ter Horst, U.S. Pat. No. 1,837,176), phenol or cresol is reacted with phosphorus oxychloride in the presence of aqueous sodium hydroxide and small quantities of organic solvents. In this process, too, the temperature profile is extremely unfavourable because the reaction temperature has to be kept at from 0° to 3° C. in order to obtain even remotely satisfactory yields.

This particular process is not new in principle, but is merely another version of the Schotten-Baumann reaction. W. Autenrieth (Chem. Ber. 30, 2369 (1897) has already used the Schotten-Baumann reaction to produce phosphoric acid esters, particularly phenols, cresols and naphthols, by reacting the aromatic hydroxy compounds with phosphorus oxychloride in the presence of 10% by weight sodium hydroxide solution.

The processes developed by Autenrieth and ter Horst are not really suitable for working on a commercial scale because they only give phosphoric acid triesters in yields of from 60 to 75% of the theoretical yield (see Comparison Examples 1 to 3). The technical difficulty of obtaining high yields of phosphoric acid triesters by the Schotten-Baumann reaction lies in the fact that the phosphorus oxychloride generally used is partly or completely hydrolysed by the aqueous sodium hydroxide and the sodium salts of the corresponding hydroxy compounds thus formed do not further react with the aromatic hydroxy compounds under the reaction conditions applied to form the phosphoric acid ester.

A process has now been found, by which it is possible, using the Schotten-Baumann reaction, to obtain yields of phosphoric acid triesters which, in most cases, amount to from 92 to 99% of the theoretical yield. This is all the more surprising insofar as, in a preferred embodiment of the process, the reaction components are mixed under high turbulence, the phosphorus oxychloride generally used as the phosphorus halogen compound being in intimate contact with the aqueous alkaline phase.

In the process according to the present invention, aromatic hydroxy compounds are reacted with phosphorus oxyhalides, phosphorus pentahalides, phosphoric acid monoester di-halides or phosphoric acid diester monohalides in the presence of aqueous metal hydroxide solutions and sufficient quantities of organic solvents to form phosphoric acid triesters, the reaction being carried out in two or more stages. The process according to the present invention is preferably applied to the reaction of aromatic hydroxy compounds with phosphorus oxychloride in the presence of an aqueous alkali metal hydroxide solution and organic water-immiscible solvents. The pH value is preferably kept in the range of from pH 7.5 to pH 13.5 during the reaction. In contrast to the process previous applied, this avoids problems of corrosion caused by the evolution of gaseous hydrogen chloride.

Accordingly, the present invention relates to a process for the production of phosphoric acid triesters corresponding to the following general formula:

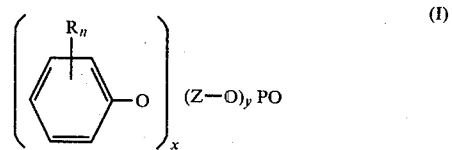  (I)

wherein

R represents a hydrogen atom, an alkyl radical containing from 1 to 20, preferably from 1 to 12 carbon atoms, an alkoxy radical containing from 1 to 20, preferably from 1 to 4 carbon atoms, a phenoxy radical, an optionally fused phenyl radical, a radical of the formula —COOR₁, where R₁ represents an alkyl group containing from 1 to 20 carbon atoms, a nitrile group or a halogen atom, for example (Cl, Br or F), n represents an integer of from 1 to 5 and the radicals R may be the same or different, x represents an integer of from 1 to 3, Z represents an alkyl radical containing from 1 to 20 carbon atoms or a radical of the following general formula:

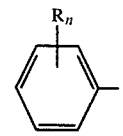

wherein

R and n are defined as above and y represents 3-x, by reacting phosphorus oxyhalides, phosphorus pentahalides, phosphoric acid monoester dihalides or phosphoric acid diester halides corresponding to the following general formulae:

ZO PO Hal₂    (II)

(ZO)₂PO Hal    (III)

wherein Z is defined as above and Hal represents Cl and/or Br, with at least one hydroxyaryl compound corresponding to the following general formula:

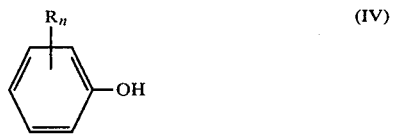

wherein R and n are defined as above, in a two-phase mixture of an organic solvent and an aqueous alkaline earth metal and/or alkali metal hydroxide solution, characterised in that the reaction is carried out in two or more stages.

Phosphorus oxychloride is preferably used as the phosphorus oxyhalide in the process according to the present invention. It is also possible to use phosphorus pentahalides, preferably phosphorus pentachloride. Phosphoric acid monoester dihalides or phosphoric acid diester halides, of the type which may be obtained, for example, by reacting phosphorus oxyhalides with a substoichiometric quantity of an organic hydroxy compound, may also be used in the process according to the present invention. Examples of these phosphoric acid halides are phosphoric acid monobutyl ester dichloride, phosphoric acid mono-2-ethyl hexyl ester dichloride and phosphoric acid diphenyl ester monochloride. Alkyl groups containing from 1 to 20, preferably from 1 to 12 carbon atoms may generally be used as alkyl in the ester group. In addition, it is possible to use hydroxyaryl compounds corresponding to formula (IV) as an esterification component.

Reactants for the above-mentioned phosphorus compounds suitable for use in the process according to the present invention are hydroxyaryl compounds corresponding to the following general formula:

wherein

R represents a hydrogen atom, an alkyl radical containing from 1 to 20, preferably from 1 to 12 carbon atoms, an alkoxy radical containing from 1 to 20, preferably from 1 to 4 carbon atoms, a phenoxy radical, an optionally fused phenyl radical, a radical of the formula —COOR$_1$, in which R$_1$ represents an alkyl group containing from 1 to 20 carbon atoms, a nitrile group or a halogen atom (for example Cl, Br or F), and n represents an integer of from 1 to 5 and the radicals R may be the same or different.

These compounds may be used either individually or in admixture in the process according to the present invention.

Suitable compounds are, for example, phenol, o-, m-, and p-cresol, o, m- and p-isopropylphenol, o-, m- and p-butylphenol, o-, m- and p-2-ethylhexylphenol, o-, m- and p-nonylphenol, 2-ethoxyphenol, 4-phenoxyphenol, 2-phenylphenol, o- and p-chlorophenol, o- and p-bromophenol, tribromophenol, α-naphthol or 4-hydroxybenzoic acid dodecyl ester. The o-, m- and p-compounds may be used either individually or in admixture.

From 1 to 1.3 mole equivalents, preferably from 1 to 1.2 mole equivalents of phosphorus halide are used per mole of hydroxyaryl compound in the reaction. (This represents for example from 1 to 1.3 moles of phosphorus oxychloride per 3 moles of hydroxyaryl compound).

The aqueous alkaline earth metal and/or alkali metal hydroxide solutions used may be lithium, sodium, potassium hydroxide, calcium hydroxide or ammonium hydroxide solutions.

Alkali metal hydroxide solutions are preferably used. It is particularly preferred to use an aqueous sodium hydroxide solution in the process according to the present invention.

The alkaline earth metal and/or alkali metal hydroxide is used in a quantity of from 1 to 1.4 equivalents, preferably in a quantity of from 1 to 1.2 equivalents per equivalent of phosphorus halide compounds. The amount of pure alkaline earth metal and/or alkali metal hydroxide in the aqueous alkaline earth metal and/or alkali metal hydroxide solutions may differ within very wide limits. Concentrations of from 5 to 50% by weight are preferred, concentrations of from 10 to 30% by weight being particularly preferred. The pH value is preferably kept at a value of from pH 7.5 to 13.5 throughout the reaction and is determined by the acidity of the hydroxyaryl compound used and of the alkaline earth metal and/or alkali metal hydroxide excess.

Preferred organic solvents are water-immiscible compounds such as benzene, toluene, xylene, chlorobenzene, dichlorobenzene, methylene chloride and chloroform. The solvent is preferably used in a quantity of from 30 to 1500% by weight and, more particularly, in a quantity of from 50 to 1000% by weight, based on the phosphorus halogen compound (starting product). Less than 30% by weight of solvent, as used, for example, in U.S. Pat. No. 1,837,176, should preferably be avoided because otherwise the yield is excessively reduced.

The reaction temperature should be in the range of from 0° to 50° C., the reaction preferably being carried out at a temperature of from 10° to 40° C. to make it easier to handle on a large scale. In general, the low reaction temperature makes it possible to obtain water-clear products which may be directly used without distillation.

The reaction times required for carrying out the process according to the present invention are very short. In most cases, the reaction is over in from 5 to 60 minutes.

In general, there is no need for catalysts to be used in the process according to the present invention because the phosphoric acid triesters are obtained in excellent yields and the reaction times are very short. In special cases, it may be advantageous to use quaternary ammonium or phosphonium compounds of the type known in the literature as phase transfer catalysts. Examples of compounds such as these are triethyl benzyl ammonium chloride, tetrabutyl ammonium chloride, tetrabutyl ammonium bromide, methyl trioctyl ammonium chloride and tributyl hexadecyl phosphonium bromide. The catalyst is preferably used in a quantity of from 0 to 1 mole per mole of hydroxyaryl compound.

By virtue of the narrow selection of reaction components in terms of quantity and concentration on which the process according to the present invention is based, but above all be virtue of the fact that the reaction is carried out in two or more stages, the yields are distinctly higher than those of the prior art. Carrying out the reaction in two or more stages is absolutely essential for the high yield to be obtained. In a single-stage reaction carried out for comparison with the multistage reaction, the yield obtained was distinctly lower (cf. Comparison Example 2). It is particularly surprising that, in the process of the present invention even where exactly molar quantities of the reactants are used, yields of more than 92% of phosphoric acid triesters are obtained.

The two-stage or multistage reaction is carried out by reacting the entire quantity of hydroxyaryl compounds together with from 30 to 95% by weight, preferably with from 50 to 90% by weight of the total quantity of the alkaline earth metal and/or alkali metal hydroxide solution to be used with from 30 to 95% by weight, preferably with from 50 to 90% by weight of the total quantity of phosphorus halogen compounds to be used under high turbulence in the presence of the water-immiscible solvent. The remaining 5 to 70% by weight, preferably 10 to 50% by weight, of alkaline earth metal and/or alkali hydroxide metal solution and the phosphorus halogen compound are then either added to the reaction mixture in a second stage, in which case the overall reaction comprises two stages, or alternatively are added in several individual portions, in which case the overall reaction comprises several stages. In most cases, a two-stage reaction is sufficient for obtaining a yield of more than 92%. For economic reasons, the reaction is generally not carried out in more than five stages.

The process according to the present invention may be carried out either continuously or in batches.

In the batch process, from 30 to 95% by weight of the total alkaline earth metal and/or alkali metal hydroxide solution are initially introduced with the total quantity of hydroxyaryl compound, after which from 30 to 95% by weight of the total phosphorus halogen compounds dissolved in organic solvents are added with vigorous stirring and thorough cooling. The remaining quantities of starting products are then separately introduced.

In one particularly suitable embodiment of the continuous process, the reaction is carried out in two or more reactors equipped with circulation pumps, followed by an after-reaction in one or more stirrer-equipped vessels. The pump-equipped reactors are designed in such a way that the reaction mixture is pumped around in a turbulent flow and thoroughly cooled. This can be achieved, for example, by a combination of adequately dimensioned rotary pumps, heat exchangers and flow tubes. From 30 to 95% by weight of the total phosphorus halogen compounds dissolved in an organic solvent and the mixture of hydroxyaryl compounds with from 30 to 95% by weight of the total alkaline earth metal and/or alkali metal hydroxide solution are continuously introduced into the first pump reactor. The mixture leaving the pump reactor is introduced into a second pump reactor where the remaining quantities of starting compounds are normally separately added. This residual quantity may optionally be distributed between several pump reactors arranged one behind the other. Following the after-reaction carried out in one or more stirrer-equipped vessels, the organic phase may be separated off and worked up.

The continuous process may also be carried out in a cascade of stirrer-equipped vessels. Admixture in the vessels may optionally be improved by additionally pumping the reaction mixture around in the vessels.

The process of the present invention is illustrated by the following Examples. All of the percentages are used on a weight basis unless otherwise indicated.

COMPARISON EXAMPLE 1

324 g (3.0 moles) of cresol (m:p=70:30) and 1200 g (3.0 moles) of 10% sodium hydroxide solution are initially introduced into a three-necked flask equipped with a dropping funnel, stirrer and thermometer, and stirred. 161 g (1.05 mole) of phosphorus oxychloride are added dropwise to this solution over a period of 1 hour with thorough cooling, the temperature being kept at from 18° to 21° C. After stirring for 1 hour at a temperature of from 20° to 23° C., the solution was extracted by repeated shaking with toluene and the organic phase distilled off. The yield of tricresyl phosphate amounted to 225 g (61.1% of the theoretical yield).

COMPARISON EXAMPLE 2

324 g (3.0 moles) of cresol (m:p=70:30), 511 g (3.0 moles) of 23.5% sodium hydroxide and 30 g of toluene were introduced into the apparatus described in Comparison Example 1 and stirred. 153.5 g (1.0 mole) of phosphorus oxychloride were added dropwise over a period of 1 hour at a temperature kept at from 0° to 3° C. by thorough cooling. On completion of the addition, the reaction mixture was kept at a temperature of from 0° to 3° C. for 3 hours and subsequently extracted by repeated shaking with toluene. 267 g (72.6% of the theoretical yield) of tricresyl phosphate were obtained after distillation.

COMPARISON EXAMPLE 3

The procedure was as described in Comparison Example 2, except that the reaction temperature was kept at from 23° to 28° C. 246 g (66.8% of the theoretical yield) of tricresyl phosphate were obtained after distillation of the organic phase.

EXAMPLE 1

324 g (3.0 moles) of cresol (m:p=70:30), 480 g (2.4 moles) of 20% sodium hydroxide and 100 g of toluene were introduced under nitrogen into the apparatus described in Comparison Example 1. A solution of 123 g (0.8 mole) of phosphorus oxychloride in 300 g of toluene was then added dropwise over a period of 30 minutes with extremely vigorous stirring, the reaction temperature being kept at from 23° to 28° C. On completion of the addition, a solution of 30.7 g (0.2 mole) of phosphorus oxychloride in 100 g of toluene and 120 g (0.6 mole) of 20% sodium hydroxide were separately added dropwise over a period of 5 minutes. The mixture was then left to react for 30 minutes at 25° C., after which the organic phase was separated off. Toluene and residues of unreacted cresol were distilled off in vacuo. 358 g (97.4% of the theoretical yield) of tricresyl phosphate were obtained in the form of an almost water-clear residue.

EXAMPLE 2

324 g (3.0 moles) of cresol (70/30), 600 g (3.0 moles) of 20% sodium hydroxide and 100 g of toluene were introduced under nitrogen into the apparatus described in Comparison Example 1. A solution of 153.5 g (1.0 mole) of phosphorus oxychloride in 400 g of toluene was added dropwise with extremely vigorous stirring over a period of 30 minutes at from 23° to 28° C. On completion of the addition, the mixture was left to react for 30 minutes at 25° C. and then worked up in the same way as described in Example 1. 323 g (87.8% of the theoretical yield) of tricresyl phosphate were obtained.

EXAMPLE 3

Solutions prepared under nitrogen of 3.73 kg of cresol (m:p=70:30) in 5.52 kg of 20% sodium hydroxide and 1.41 kg of phosphorus oxychloride in 4.6 kg of toluene were continuously introduced hourly into a pump reactor equipped with a rotary pump and a heat exchanger. The average residence time of the reaction mixture set in turbulent motion was 25 minutes and the reaction temperature was kept at from 25° to 30° C. The product leaving the reactor was transferred to a second pump reactor into which a solution of 0.36 kg/h of phosphorus oxychloride in 1.15 kg/h of toluene and 1.38 kg/h of 20% sodium hydroxide solution were additionally introduced. The average residence time in the second reactor was 5 minutes. The after-reaction was carried out at 25° C. in a stirrer-equipped vessel with an average residence time of 20 minutes. The aqueous phase was separated off and toluene together with small quantities of residual cresol were distilled off from the organic phase, leaving 4.14 kg/h of tricresyl phosphate (98.1% of the theoretical yield) in the form of an almost water-clear residue.

EXAMPLES 4 TO 11

The procedure adopted in these Examples was the same as that described in Example 1

| Aromatic hydroxy compound | Phosphoric acid ester | Rection stage I | Reaction stage II | Yield (% of the theoretical yield) |
|---|---|---|---|---|
| (4) cresol (m:p=70:30) | tricresyl phosphate | 3.0 moles cresol/2.6 moles NaOH (20%), 0.8 mole POCl$_3$/500 g methylene chloride | 0.6 mole NaOH (20%), 0.25 mole POCl$_3$/100 g methylene chloride | 98.5 |
| (5) cresol (m:p=70:30) | tricresyl phosphate | 3.0 moles cresol/2.3 moles NaOH (23%),0.7 mole POCl$_3$/400 g toluene | 1.0 mole NaOH (23%), 0.4 mole POCl$_3$/200 g toluene | 97.1 |
| (6) phenol | triphenyl phosphate | 3.0 moles phenol/2.4 moles NaOH (20%), 0.8 mole POCl$_3$/500 g toluene | 0.6 mole NaOH (20%), 0.2 mole POCl$_3$/100 g toluene | 96.0 |
| (7) phenol, cresol | diphenyl cresyl phosphate | 2.0 moles phenol, 1.0 mole cresol/2.5 moles NaOH (20%), 0.8 moles POCl$_3$/500 g toluene | 0.6 mole NaOH (20%), 0.2 mole POCl$_3$/100 g toluene | 96.5 |
| (8) m-isopropyl-phenol | triisopropyl-phenyl phosphate | 3.0 moles m-isopropylphenol/2.5 moles NaOH (20%),0.8 mole POCl$_3$/500 g toluene | 0.6 mole NaOH (20%), 0.2 mole POCl$_3$/100 g toluene | 94.9 |
| (9) phenol, m-isopropyl phenol | mono-isopropyl phenyl diphenyl phosphate | 2.0 moles phenol, 1.0 mole m-isopropylphenol/2.5 moles NaOH (20%), 0.8 mole POCl$_3$/500 g toluene | 0.6 mole NaOH (20%), 0.2 mole POCl$_3$/100 g toluene | 95.8 |
| (10) phenol, m-isopropyl-phenol | diisopropyl-phenyl phenyl-phosphate | 1.0 mole phenol, 2.0 moles m-isopropylphenol/2.5 moles NaOH (20%), 0.8 mole POCl$_3$/500 g toluene | 0.6 mole NaOH (20%), 0.2 mole POCl$_3$/100 g toluene | 95.9 |
| (11) phenol | diphenyl-2-ethyl-hexyl phosphate | 2.0 moles phenol/1.6 moles NaOH (20%), 0.8 mole phosphoric acid-2-ethylhexyl ester dichloride/500 g toluene | 0.5 mole NaOH (20%), 0.2 mole phosphoric acid-2-ethyl-hexyl ester dichloride/100 g toluene | 97.0 |

We claim:
1. A process for the production of phosphoric acid triesters corresponding to the formula:

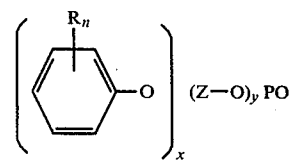

wherein

R represents hydrogen, alkyl containing from 1 to 20 carbon atoms, alkoxy containing from 1 to 20 carbon atoms, phenoxy, an optionally fused phenyl radical, and —$COOR_1$, where $R_1$ represents an alkyl containing from 1 to 20 carbon atoms, a nitrile or a halogen atom, n represents an integer of from 1 to 5 and each R may be the same or different, x represents an integer of from 1 to 3, Z represents an alkyl containing from 1 to 20 carbon atoms or the formula:

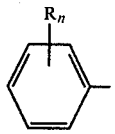

wherein

R and n are defined as above and y represents 3-x, said process comprising reacting phosphorus oxyhalides, phosphorus pentahalides, phosphoric acid monoester dihalides or phosphoric acid diester halides corresponding to the formula:

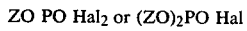

ZO PO $Hal_2$ or $(ZO)_2$PO Hal wherein Z is defined as above and Hal represents Cl and/or Br. with at least one hydroxyaryl compound of the formula:

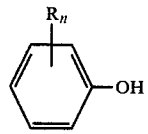

wherein R and n are defined as above, in a two-phase mixture of an organic solvent, an aqueous alkaline earth metal and/or alkali metal hydroxide solution, characterized in that the reaction is carried out in stages comprising the steps of reacting the entire quantity of hydroxyaryl compounds with from 30 to 95% by weight of the total quantity of the alkaline earth metal and/or alkali metal hydroxide solution to be used with from 30 to 95% by weight of the total quantity of phosphorus halogen compounds to be used under high turbulence in the presence of the water-immiscible solvent, as a first stage and then adding the remaining 5 to 70% by weight of alkaline earth metal and/or alkali hydroxide metal solution and the phosphorus halogen compound to the reaction mixture as one or more individual portions.

2. A process as claimed in claim 1, characterised in that the reaction is carried out at a temperature in the range of from 0° to 50° C.

3. A process as claimed in claim 1, characterised in that the reaction is carried out at a temperature of from 10° to 40° C.

4. A process as claimed in claim 1, characterised in that from 1 to 1.3 mole equivalents of phosphorus halogen compound are used per mole of hydroxyaryl compound.

5. A process as claimed in claim 1, characterised in that from 1 to 1.4 equivalents of alkaline earth metal and/or alkali metal hydroxide are used per equivalent of phosphorus halide compound.

6. A process as claimed in claim 1, characterised in that phosphorus oxychloride or 2-ethylhexyl phosphoric acid dichloride is used.

7. A process as claimed in claim 1, characterised in that an alkaline earth metal and/or alkali metal hydroxide solution having a concentration of from 5 to 50% by weight is used.

8. A process as claimed in claim 1, characterised in that the reaction is carried out in from two to five stages.

9. A process as claimed in claim 1 characterized in that the total quantity of hydroxyaryl compound, from 50 to 90% by weight of the total quantity of alkaline earth metal and/or alkali metal hydroxide solution to be used and from 50 to 90% by weight of the total quantity of phosphorus halide compound to be used are reacted with one another and the remainder of the reactants subsequently added and reacted.

* * * * *